(12) United States Patent
Buchalter

(10) Patent No.: US 11,813,366 B2
(45) Date of Patent: Nov. 14, 2023

(54) NATURAL BABY DIAPER INCLUDING BAMBOO FIBER

(71) Applicant: Products On The Go, LLC, Delray Beach, FL (US)

(72) Inventor: Sharon Buchalter, Delray Beach, FL (US)

(73) Assignee: Products On The Go, LLC, Delray Beach, FL (US)

( * ) Notice: Subject to any disclaimer, the term of this patent is extended or adjusted under 35 U.S.C. 154(b) by 814 days.

(21) Appl. No.: 16/721,674

(22) Filed: Dec. 19, 2019

(65) Prior Publication Data

US 2020/0197560 A1 Jun. 25, 2020

Related U.S. Application Data

(60) Provisional application No. 62/782,171, filed on Dec. 19, 2018.

(51) Int. Cl.
| | |
|---|---|
| *A61L 15/40* | (2006.01) |
| *A61F 13/511* | (2006.01) |
| *A61F 13/49* | (2006.01) |
| *A61F 13/56* | (2006.01) |
| *A61F 13/15* | (2006.01) |
| *A61F 13/514* | (2006.01) |
| *A61F 13/53* | (2006.01) |
| *A61F 13/494* | (2006.01) |

(52) U.S. Cl.
CPC ......... *A61L 15/40* (2013.01); *A61F 13/49011* (2013.01); *A61F 13/49406* (2013.01); *A61F 13/51121* (2013.01); *A61F 13/5633* (2013.01); *A61F 2013/15943* (2013.01); *A61F 2013/49074* (2013.01); *A61F 2013/51452* (2013.01); *A61F 2013/530481* (2013.01)

(58) Field of Classification Search
CPC .......... A61F 13/15252; A61F 13/51121; A61F 2013/15943; A61F 2013/49074; A61F 2013/530481; A61F 13/511; A61F 13/49; A61F 13/56; A61F 13/15; A61F 13/514; A61F 13/53; A61F 13/494; A61L 15/40
See application file for complete search history.

(56) References Cited

U.S. PATENT DOCUMENTS

| | | | | |
|---|---|---|---|---|
| 2003/0139720 | A1* | 7/2003 | Nordness | A61F 13/49 604/385.01 |
| 2014/0330231 | A1* | 11/2014 | Zavala | A61L 15/18 604/360 |
| 2017/0021051 | A1* | 1/2017 | Richards | A61F 13/53409 |

(Continued)

FOREIGN PATENT DOCUMENTS

| | | | | |
|---|---|---|---|---|
| CA | 3036923 | * | 3/2022 | ............. A61F 13/49 |
| WO | 2019199154 | * | 10/2019 | ........... A61F 13/505 |

*Primary Examiner* — Michele Kidwell
(74) *Attorney, Agent, or Firm* — Workman Nydegger

(57) ABSTRACT

Disclosed are natural baby products and related methods of use. Disposable baby hygiene products, particularly disposable baby hygiene products made with natural, sustainable, environmentally-responsible, and/or biodegradable materials include disposable baby diapers made with bamboo and other natural, sustainable, environmentally-responsible, and/or biodegradable materials and disposable baby swim diapers made with natural, sustainable, environmentally-responsible, and/or biodegradable materials.

9 Claims, 11 Drawing Sheets

(56) References Cited

U.S. PATENT DOCUMENTS

| | | | | |
|---|---|---|---|---|
| 2018/0140469 A1* | 5/2018 | Kane | ................. | A61F 13/15252 |
| 2019/0151165 A1* | 5/2019 | Cannon | ............. | A61F 13/49004 |
| 2021/0330519 A1* | 10/2021 | Monroe | .................. | A61F 13/49 |

* cited by examiner

| Position | Dimensions/Description |
|---|---|
| A | Chassis Length 462 mm |
| B | Chassis Width 218 mm |
| C | Landing Zone 45 x 168 mm |
| D | Closure Tab |
| E | Stretch Closure Tab |
| F | Stretch Waist 50 x 140 mm (extended) |
| G | Landing Zone Offset from End 21 mm |
| H | Closure Tab Offset from End 10 mm |
| I | Wetness Indicator 220 mm (Offset 111 & 131 mm) |

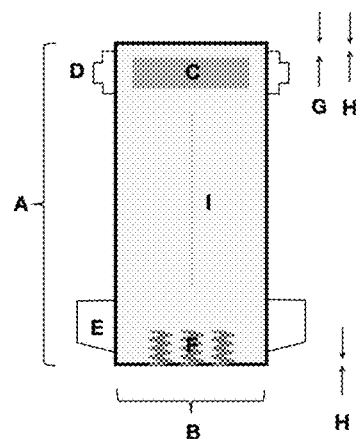

FIG. 3

| Position | Dimensions/Description |
|---|---|
| J | Core Length 395 mm |
| K | Core Width 110 mm (90 mm center) |
| D | Closure Tab |
| E | Stretch Closure Tab |
| L | Acquisition & Distribution Layer 63 x 230 mm |
| M | Inner Leg Gathers 30 mm x full length |
| N | Two Strands of Spandex (Offset 25 & 60 mm) |
| O | Two Strands of Spandex (Offset 60 & 90 mm) |
| P | Wide Core Section Length 100 mm |

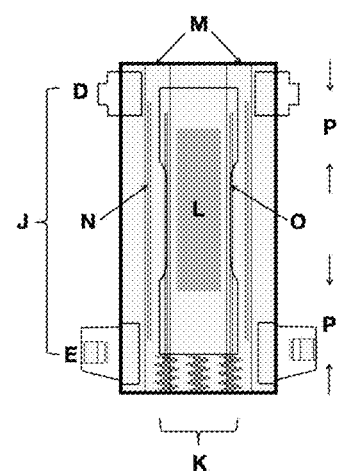

FIG. 4

NATURAL BABY DIAPER INCLUDING BAMBOO FIBER

BACKGROUND

1. Technical Field

The present disclosure relates to disposable baby hygiene products, particularly disposable baby hygiene products made with natural, sustainable, environmentally-responsible, and/or biodegradable material(s). Specifically, the present disclosure relates to disposable baby diapers made with bamboo and other natural, sustainable, environmentally-responsible, and/or biodegradable material(s) and disposable baby swim diapers made with natural, sustainable, environmentally-responsible, and/or biodegradable material(s).

2. Related Technology

Infants and young children generally have a difficult time controlling their bodily functions, such as urination and bowel movements, and articulating when they need to use the bathroom. For this reason, parents and caregivers rely on diapers to contain mess when accidents occur. For centuries, absorbent materials have been used for infant and toddler hygiene care. Traditionally, cloth diaper materials consisted of a folded square or rectangle of linen cloth and were secured with clips or safety pins. In the early part of the 20$^{th}$ century, people became aware of the potential for infection from the bacteria in diaper waste and began to boil cloth diapers to sterilize them. In the 1960s, disposable diapers rapidly took hold due to their ease of use and more sanitary nature and reusable cloth diapers fell out of favor.

While disposable diapers offer convenience, they do have several dangerous environmental drawbacks. Each year, more than 200,000 trees are lost to the manufacture of disposable diapers for babies in the U.S. alone. In addition, it takes 3.4 billion gallons of fuel oil every year to make diapers. Disposable diapers use 20 times more raw materials, two times more water, and three times more energy to make than cloth diapers. In addition to depleting natural resources, the manufacture of disposable diapers relies on non-renewable energy sources. A single disposable diaper takes over 500 years to decompose in a landfill, and the decomposition process allows volatile organic compounds to be released into the air and surrounding land area.

Not only do disposable diapers account for a substantial amount of trash in U.S. landfills, but they also pose serious risks to the environment and people alike. Diapers are typically treated with chemicals, and often contain dyes and dioxin, which is formed as a byproduct of the chlorine bleaching process. For example, sodium polyacrylate is supposed to stay in the core of a standard disposable diaper to increase absorbency, however, it has been found to leak through the lining, leaving small transparent crystals on the baby's skin. Soft, sensitive skin of babies is prone to rashes and allergic reactions due to the chemicals that typically are included in disposable baby diapers.

The National Center for Health Statistics reported that just shy of 4 million babies were born in 2015. One baby is estimated to use 1,500 to 1,800 disposable diapers per year. As a result, the Environmental Protection Agency reports that about 20 billion disposable diapers are dumped in landfills each year, accounting for more than 3.5 million tons of waste. Accordingly, there are a number of disadvantages with disposable diapers that can be addressed.

Diapers are typically engineered for their absorbent qualities; however, these absorbent properties are limiting in certain situations. For example, standard absorbent diapers are not ideal for use in wet environments, particularly pools, lakes, and other large bodies of water while engaging in activities such as swimming Standard diapers absorb the surrounding water and become heavy for the wearer, as well as ineffective. In these cases, non-absorbent swim diapers are used.

The purpose of a swim diaper is to contain solid waste, while the lack of absorbency prevents the diaper from swelling when submerged in water, it also will not absorb urine or loose waste. If a normal diaper gets wet in a pool it will swell up and will continue to inflate with water until it bursts, which may result in the release of harmful fecal matter into the pool. Sick children who are not potty-trained and do not wear swim diapers may be responsible for the transmission of *E. coli* from fecal matter. Many pools require infants and young children to wear swim diapers to prevent the spread of illness from germs contained in fecal matter. These swim diapers may be worn underneath a bathing suit or as a bathing suit by babies or young children. Swim diapers prevent the spread of solid waste in bodies of water and contain accidents until a parent or caregiver is able to change the infant or young child's diaper.

Swim diapers can be reusable or disposable. Reusable swim diapers are often lined with a fiber which encourages solid waste to cling to the fiber without an absorbency layer. Some swim diapers use polyester or neoprene as their material. The disadvantage of reusable diapers is that they must be washed to be reused. Because reusable diapers must be washed before they can be reused, and because doing this in a sanitary manner may not be feasible in a public place, disposable diapers provide a sufficient, hygienic alternative.

Disposable swim diapers are made with water resistant and waterproof properties in order to be effective. However, many of these waterproof and water-resistant materials are not typically biodegradable. Accordingly, disposable swim diapers may only be partially biodegradable and, therefore, contribute to landfill waste. Moreover, disposable swim diapers must be purchased for each and every use. While disposable diapers offer convenience, they do have several dangerous environmental drawbacks. Accordingly, there are a number of disadvantages with swim diapers that can be addressed.

BRIEF DESCRIPTION OF THE DRAWINGS

Various embodiments of the present disclosure will be discussed with reference to the appended drawings. It is appreciated that the drawings depict only typical embodiments of the presents disclosure and are not to be considered limiting of its scope.

FIG. 3 illustrates a specification sheet and corresponding model of a diaper outer in accordance with an embodiment of the present disclosure.

FIG. 4 illustrates a specification sheet and corresponding model of a diaper inner in accordance with an embodiment of the present disclosure.

BRIEF SUMMARY

Figure 1:
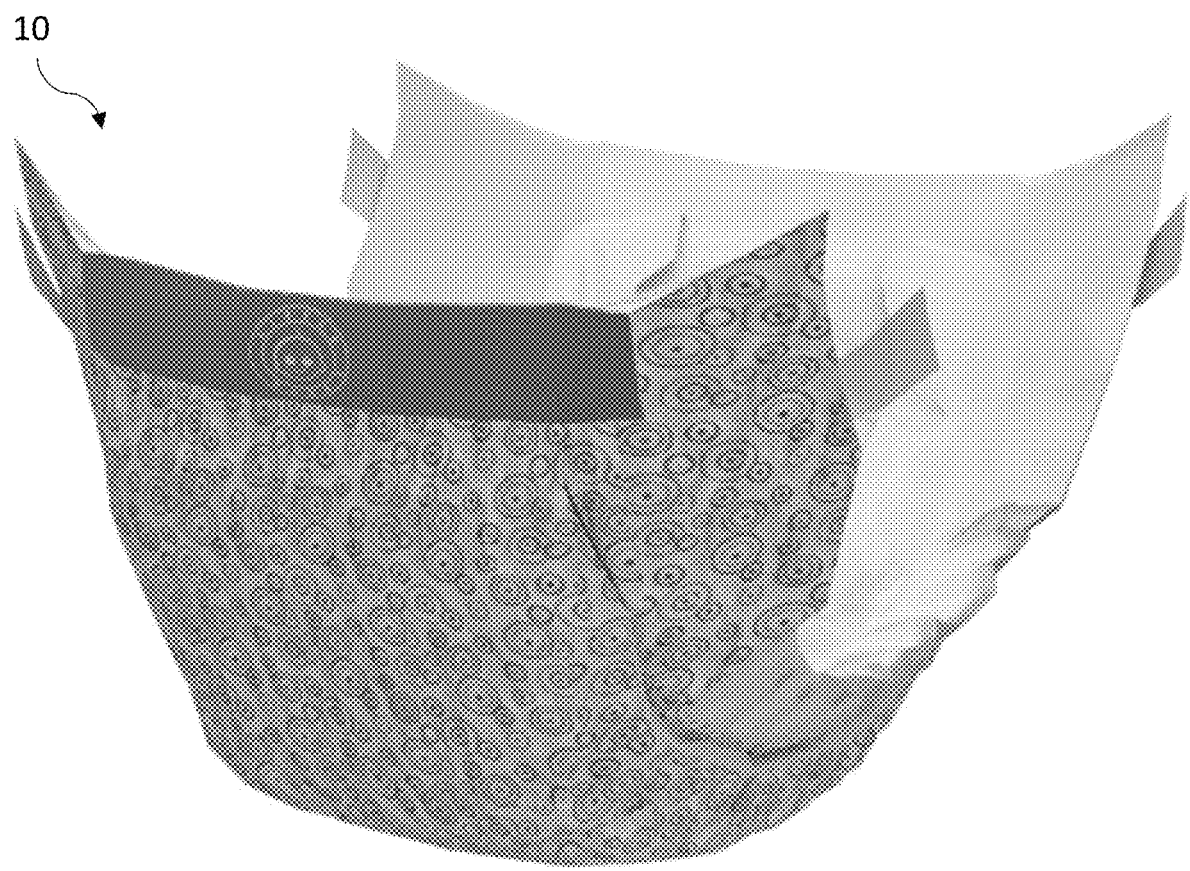
FIG. 1 illustrates a disposable baby diaper in accordance with an embodiment of the present disclosure.

Embodiments, implementations, and/or aspects of the present disclosure solve one or more of the foregoing or other problems in the art with disposable baby hygiene products, particularly disposable baby hygiene products made with natural, sustainable, environmentally-responsible, and/or biodegradable material(s). Specifically, certain embodiments, implementations, and/or aspects of the present disclosure include disposable baby diapers made with bamboo and other natural, sustainable, environmentally-responsible, and/or biodegradable material(s). Certain embodiments, implementations, and/or aspects of the present disclosure include disposable baby swim diapers made with natural, sustainable, environmentally-responsible, and/or biodegradable material(s).

Some embodiments includes a natural baby diaper, comprising: a top sheet comprising 100% bamboo fiber; a back sheet comprising 100% bamboo fiber; an absorbent core disposed between the top sheet and the back sheet, the absorbent core comprising super absorbent polymer (SAP); and, optionally, an acquisition distribution layer (ADL) covering the absorbent core, wherein the diaper is substantially free or devoid of chlorine, alcohol, perfume or fragrance, phthalate, latex, epoxy, polyvinyl chloride (PVC), tributyltin (TBT), bisphenol (BPA), 2-mercaptobenzothiazole (MBT), dibenzothiophene (DBT), antioxidant, surfactants, detergents, and/or preservative. In some embodiments, the diaper further comprises: an elastic waistband; side leakage guards; and/or a (pair of side) fastener(s).

Some embodiments includes a natural baby diaper, comprising: a top sheet, forming an exterior of the diaper; a back sheet, lining an interior of the top sheet; wherein the top sheet and back sheet form a dumbbell shape of the diaper; an absorbent core situated in a seat portion of the diaper to collect fluids and/or waste; an ADL covering the absorbent core; a front tape on an anterior portion of an outer side of the top sheet; one or more side fasteners affixed to one or more sides of the diaper; an elastic back waistband on a top of a posterior portion of the diaper; and one or more side leakage guards surrounding one or more extremity openings. In some embodiments, the natural baby diaper is disposable.

Some embodiments includes a natural baby diaper, comprising: a top sheet, forming an exterior of the diaper; a back sheet, lining an interior of the top sheet; an absorbent core situated in a seat portion of the diaper to collect fluids and waste; one or more side fasteners affixed to one or more sides of the diaper; and a back waistband on a top of a posterior portion of the diaper, wherein the diaper is made of biodegradable materials and wherein the biodegradable materials of the diaper include bamboo.

Some embodiments includes a natural disposable swim diaper, comprising: a diaper body having a waist loop at a top portion of the diaper body and a first leg loop and a second leg loop at a bottom portion of the diaper body, wherein the diaper body comprises: a top sheet comprising an outermost layer of the diaper body; a front tape pattern overlaid on the top sheet; a back sheet comprising the interior side of the diaper body; an absorbent core, wherein the absorbent core in contained between the top sheet and the back sheet; and a waistband positioned on the waist loop, wherein the diaper body is made of natural materials. In some embodiments, the absorbent core is wrapped airlaid tissue. In some embodiments, the airlaid tissue is devoid of SAP. In some embodiments, the waistband comprises an elastic material. In some embodiments, all of the materials are natural materials.

Embodiments of the present disclosure improve upon existing diapers by using an absorbent, moisture-wicking, 100% bamboo top sheet over an ultra-absorbent core comprises of next-generation, super absorbent polymer mixed with (softwood) fluff pulp, to achieve a diaper with an absorption capacity over 20-times its dry weight (e.g., 23.5× absorption capacity, on average), which existing diapers have not achieved.

Embodiments of the present disclosure further improve upon existing diapers by increasing the area of the hooks in the fastening system, increasing the density of hooks per square inch, arranging the hooks in non-continuous rows, implementing a design in which the hook is compatible to loop design, and/or by reinforcing the tabs with nonwoven material and with a hot melt construction adhesive (so that it does not break when pulled too hard or very quickly), to increase the durability of the diaper compared to existing diapers.

Embodiments of the present disclosure further improve upon existing diapers by avoiding the use of irritants, including harsh chemicals, such as chlorine, alcohol, perfumes or fragrances, phthalates, parabens, latex, epoxy, polyvinyl chloride (PVC), tributyltin (TBT), bisphenol (BPA), 2-mercaptobenzothiazole (MBT), dibenzothiophene (DBT), sugar cane, wheat or wheat by-products, corn or corn by-products, antioxidants, surfactants, detergents, and/or preservatives, which have been shown to cause dermatitis and/or other skin reactions, especially in babies with sensitive skin.

Some embodiments of the present disclosure improve upon existing swim diapers with a construction, configuration, and/or design in which the bottom (pocket) of the diaper is expanded, rounds, and/or bulbous, which improves retention, but without sacrificing comfort, due to the naturally soft materials used in manufacturing the diapers.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of exemplary embodiments of the present disclosure will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

It is also noted that each of the foregoing, following, and/or other features described herein represent a distinct embodiment of the present disclosure. Moreover, combinations of any two or more of such features represent distinct embodiments of the present disclosure. Such embodiments can also be combined in any suitable combination and/or order without departing from the scope of this disclosure. Thus, each of the features described herein can be combinable with any one or more other features described herein in any suitable combination and/or order. Accordingly, the present disclosure is not limited to the specific combinations of exemplary embodiments described in detail herein.

DETAILED DESCRIPTION

Before describing various embodiments of the present disclosure in detail, it is to be understood that this disclosure is not limited to the specific parameters and description of the particularly exemplified systems, methods, and/or products that may vary from one embodiment to the next. Thus, while certain embodiments of the present disclosure will be described in detail, with reference to specific features (e.g., configurations, parameters, properties, steps, components, ingredients, members, elements, parts, and/or portions, etc.), the descriptions are illustrative and are not to be construed as limiting the scope of the present disclosure and/or the claimed invention. In addition, the terminology used herein is for the purpose of describing the embodiments, and is not necessarily intended to limit the scope of the present disclosure and/or the claimed invention.

While the detailed description is separated into sections, the section headers and contents within each section are not intended to be self-contained descriptions and embodiments. Rather, the contents of each section within the detailed description are intended to be read and understood as a collective whole where elements of one section may pertain to and/or inform other sections. Accordingly, embodiments specifically disclosed within one section may also relate to and/or serve as additional and/or alternative embodiments in another section having the same and/or similar systems, devices, methods, and/or terminology.

Abbreviated List of Defined Terms

To assist in understanding the scope and content of the foregoing and forthcoming written description and appended claims, a select few terms are defined directly below. Unless defined otherwise, all technical and scientific terms used herein have the same meaning as commonly understood by one of ordinary skill in the art to which the present disclosure pertains.

The terms "comprising," "comprise," "comprises," and similar terms, as used herein, including in the claims, shall be inclusive and/or open-ended and do not exclude additional, un-recited elements or method steps, illustratively. Additionally, the terms "including," "having," "involving," "containing," "characterized by," variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

As used herein, the transitional phrases "consisting of," "consist of," and similar terms shall be close-ended so as to exclude additional, un-recited elements or method steps, illustratively.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim of this disclosure is not intended to be interpreted to be equivalent to "comprising."

As used herein, the terms "about," "approximately," and similar terms, with regard to a value, mean+/−10% of the stated value or amount represented thereby. For instance, throughout the present disclosure, the term "about" is used in connection with a percent concentration or composition of a component or ingredient (e.g., in a composition, formulation, or mixture, such as a fluid or liquid mixture, aqueous mixture, solution, etc., optionally or preferably measured as a w/w percent, w/v percent, v/v percent, etc.). In such instance, the term "about" and/or the term "+/−10%" implies and/or includes +/−10% of the stated numeric value, as opposed to +/−10 percentage points of the recited percent. By way of example, where 20% w/w of a component or ingredient reflects 20 g of the component or ingredient per 100 mL of total mixture, the term "about" and/or the term "+/−10%" implies and/or includes a recited range from 18 g to 22 g (i.e., from 18% w/w to 22% w/w), not a range of 10% w/w to 30% w/w. Alternatives for so-called "about" values and/or +1-10% include +/−1%, +/−2%, +/−3%, +/−4%, +/−5%, +/−6%, +/−7%, +/−8%, or +/−9% of the stated value, each of which is contemplated as a suitable alternative to or substitute for the term "about" or the use of +/−10% herein.

It will also be appreciated that where two or more values, or a range of values (e.g., less than, greater than, at least, and/or up to a certain value, and/or between two recited values) is disclosed or recited, any specific value or range of values falling within the disclosed values or range of values is likewise disclosed and contemplated herein. Thus, disclosure of an illustrative measurement (e.g., volume, concentration, etc.) that is less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 units, between 8 units and 2 units, between 6 units and 4 units, and/or any other range of values between 0 and 10 units.

As used herein, the term "substantially devoid," "substantially free," and similar terms mean (1) an undetectable or unquantifiable amount, (2) less than or below an amount generally considered by those skilled in the art to reflect a detectable or quantifiable amount, and/or (3) less than or below an amount generally considered by those skilled in the art to be functional or able to achieve a (desired or expected) result.

In at least one embodiment, the terms "form," "forming," and the like (e.g., "formed of," "formed with,"), as well as "made of" and "made with" are open-ended, such that sub-components that (are combined, mixed, or included together so as to) form a component (e.g., system, application, product, composition, mixture, ingredient, element, part, etc.) do not necessarily constitute the entire component. Accordingly, a product can be formed of, made of, formed with, or made with one or more components without, necessarily, consisting, either entirely or essentially, of said one or more components. Similarly, a component can comprise, be formed of, made of, formed with, or made with one or more sub-components, without, necessarily, consisting, either entirely or essentially, of said sub-components.

As used herein, the term "composition" includes products, formulations, and mixtures, as well as devices, apparatus, assemblies, kits, and so forth. Similarly, the term "method"

includes processes, procedures, steps, and so forth. The terms "formulation" and "composition" may be used interchangeably herein, except where context clearly indicates otherwise.

As used herein, the term "method" also contemplates processes, procedures, steps, and so forth. Moreover, the term "products" also contemplates systems, compositions, kits, and so forth.

Various aspects of the present disclosure, including systems, methods, and/or products may be illustrated with reference to one or more embodiments or implementations, which are exemplary in nature. As used herein, the terms "embodiment" and implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the description thereof.

It is noted that embodiments of the present disclosure can comprise one or more combinations of two or more of the features described herein. As used herein, "feature(s)" and similar terms can include, for example, one or more compositions, ingredients, components, elements, members, parts, portions, systems, methods, steps, configurations, parameters, properties, or other aspect of the subject matter at hand. Embodiments can include any of the features, options, and/or possibilities set out elsewhere in the present disclosure, including in other aspects or embodiments of the present disclosure. It is also noted that while each of the foregoing, following, and/or other features described herein represents a distinct embodiment of the present disclosure, features can also be combined and/or combinable with another one or more other features in any suitable combination and/or order, with or without one or more additional features included therewith or performed therebetween, to form unique embodiments, each of which is contemplated in the present disclosure. Such combinations of any two or more of such features represent distinct embodiments of the present disclosure. Accordingly, the present disclosure is not limited to the specific combinations of exemplary embodiments described in detail herein and disclosure of certain features relative to a specific embodiment of the present disclosure should not be construed as limiting application or inclusion of said features to the specific embodiment.

In addition, unless a feature is described as being requiring in a particular embodiment, features described in the various embodiments can be optional and may not be included in other embodiments of the present disclosure. Moreover, unless a feature is described as requiring another feature in combination therewith, any feature herein may be combined with any other feature of a same or different embodiment disclosed herein. Likewise, any steps recited in any method described herein and/or recited in the claims can be executed in any suitable order and are not necessarily limited to the order described and/or recited, unless otherwise stated (explicitly or implicitly). Such steps can, however, also be required to be performed in a particular order in certain embodiments of the present disclosure.

As used throughout this application the words "can" and "may" are used in a permissive sense (i.e., meaning having the potential to), rather than the mandatory sense (i.e., meaning must).

The word "or" as used herein means any one member of a particular list and also includes any combination of members of that list.

As used in this specification and the appended claims, the singular forms "a," "an" and "the also contemplate plural referents, unless the context clearly dictates otherwise. Thus, for example, reference to a "layer" includes one, two, or more layers. Similarly, reference to a plurality of referents should be interpreted as comprising a single referent and/or a plurality of referents unless the content and/or context clearly dictate otherwise. Thus, reference to "layers" does not necessarily require a plurality of such layers. Instead, it will be appreciated that independent of conjugation; one or more layers are contemplated herein.

As used herein, directional terms, such as "top," "bottom," "left," "right," "up," "down," "upper," "lower," "proximal," "distal" and the like are used herein solely to indicate relative directions and are not otherwise intended to limit the scope of the disclosure and/or claimed invention.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

As used herein, the terms "baby diaper(s)," "baby nappy," and so forth are illustrative/exemplary of any form of diaper or nappy, including but not limited to toddler diapers and/or nappies, adolescent diapers and/or nappies, adult diapers and/or nappies, and so forth.

As used herein, the term "natural" refers to organic products, products derived from plants, minimally processed products generally known to be non-toxic for at least topical applications, and the like.

As used herein, "nonwoven" fabric and similar terms refers to a fabric-like material made from staple fibre (short) and long fibres (continuous long), bonded together by chemical, mechanical, heat or solvent treatment. The term generally includes non-knitted fabrics, as well. Nonwovens are typically manufactured by putting small fibers together in the form of a sheet or web (similar to paper on a paper machine), and then binding them either mechanically (as in the case of felt, by interlocking them with serrated needles such that the inter-fiber friction results in a stronger fabric), with an adhesive, or thermally (by applying binder (in the form of powder, paste, or polymer melt) and melting the binder onto the web by increasing temperature). Nonwovens include, for example, staple nonwovens, melt-blown nonwovens, spunlaid, spunbond, flashspun, Air-laid, and the like.

By "Quantum satis" (also referred to as "q.s." or "qs") is meant the amount that is enough. Accordingly, a component or ingredient "qs 100%," "provided at qs 100%," or "qs to 100%" indicates that the component or ingredient is provided or included in an amount sufficient to complete the composition or to bring the total (of all components, whether recited or not) to 100%. It is noted, however, that a (final) component or ingredient "qs 100%," "provided at qs 100%," or "qs to 100%" does not indicate that the mixture consists of, consists essentially of, or only contains the components listed or recited immediately before the "qs 100%" component. In other words, "qs 100%," and similar terms, is meant to be an open-ended expression indicating the source of the remainder, whatever that remainder may be.

To facilitate understanding, like references (i.e., like naming of components and/or elements) have been used, where possible, to designate like components and/or elements common to the written description and/or figures. Specific language will also be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential).

The headings used herein are for organizational purposes only and are not meant to be used to limit the scope of the description or the claims.

Illustrative Embodiments

The following description of illustrative embodiments includes disclosure that is relevant to one or more aspects or embodiments of the present disclosure. Accordingly, some embodiments of the present disclosure can include the combination of elements or features disclosed in the following examples. It is noted, however, that various aspects or embodiments of the present disclosure need not, may not, or do not include each and every element or feature disclosed in a particular example. Indeed, certain aspects or embodiments may have fewer than all of the exemplary elements or features disclosed in connection with the following illustrative embodiments without departing from the scope of the present disclosure. In addition, some aspects or embodiments may include one or more elements or features disclosed in a separate aspect or embodiment. In other words, elements or features disclosed in one or more of the following examples can be included and/or incorporated into any one or more of the embodiments disclosed herein.

Disclosed herein are embodiments of natural, disposable baby hygiene products, or disposable baby hygiene products made with natural, sustainable, environmentally-responsible, and/or biodegradable material(s). Specifically, certain embodiments of the present disclosure include disposable baby diapers made with bamboo and other natural, sustainable, environmentally-responsible, and/or biodegradable material(s). Additional or alternative embodiments include disposable baby swim diapers made with natural, sustainable, environmentally-responsible, and/or biodegradable material(s).

Embodiments of the present disclosure enable a baby diaper that is disposable and made of sustainable materials and that biodegrades once it is discarded, thereby decreasing landfill waste. The baby diaper may be free of irritating and/or harmful materials, for example, the baby diaper may be substantially free or devoid (preferably 100% free) of chlorine, alcohol, perfumes or fragrances, phthalates, parabens, latex, epoxy, polyvinyl chloride (PVC), tributyltin (TBT), bisphenol (BPA), 2-mercaptobenzothiazole (MBT), dibenzothiophene (DBT), sugar cane, wheat or wheat by-products, corn or corn by-products, antioxidants, surfactants, detergents, and/or preservatives. The baby diaper may be naturally hypoallergenic and/or antibacterial.

Natural Bamboo Diapers

Sustainable and/or biodegradable materials incorporated into various embodiments may include bamboo. Without being bound to any particular theory, bamboo materials are naturally derived from the bamboo plant, and the bamboo plant itself regenerates quickly once parts of the plant are harvested, rendering its use both economical and sustainable. Bamboo has natural deodorizing and antibacterial properties and is naturally hypoallergenic. Bamboo is made of soft fibers that are naturally smooth and round and is naturally moisture and thermal regulating. Importantly, bamboo is 70% more absorbent than cotton and wicks moisture (away from its surface and away from the body to keep babies drier than cotton). Environmentally, bamboo generates 30% more oxygen than other plants and trees, grows without the need for irrigation, pesticides, or fertilizers, and, decomposes naturally (reducing the time it takes for a diaper made with bamboo to decompose in a landfill— from 500 years for a conventional diaper to 180 days).

In one or more embodiments, a natural and/or disposable diaper can comprise a top sheet comprising 100% bamboo fiber, a back sheet comprising 100% bamboo fiber, and an absorbent core layer disposed between the top sheet and the back sheet, the absorbent core comprising a mixture of (softwood) fluff pulp and super absorbent polymer (SAP). The mixture of SAP and fluff pulp is configured and adapted to absorb high amounts of liquid, locking the liquid into the core layer. The unique combination of ultra-absorbent core sandwiched between moisture-wicking, 100% bamboo fiber sheets provides a higher degree of absorptive capacity than found in existing (leading) diapers.

In some embodiments, the tops sheet of the diaper may be, comprise, be comprised of, consist essentially of, or consist of bamboo (e.g., 100% bamboo, a 100% bamboo sheet (material), or a 100% bamboo pulp material). The top sheet can be naturally soft and comfortable to contact (skin). The top sheet can also be untreated (e.g., with surfactants and/or detergents). Some embodiments can include a liner (e.g., lining the top sheet). The liner may comprise, include, incorporate or be made or formed of aloe. In some embodiments the bamboo top sheet may include the liner.

The back sheet may be a water-resistant outer layer preventing liquids from leaking out of the diaper. The back sheet may be made of 100% biodegradable material. An example of a suitable biodegradable material is bamboo. Preferably, the back sheet comprises 100% bamboo fiber material. In some embodiments, the top sheet and/or back sheet form a dumbbell shape of the diaper. In some embodiments, the top sheet and/or back sheet may have an hourglass shape.

The absorbent core layer can include a super absorbent polymer (SAP). SAP can absorb water up to several hundred times of its own weight and turn into a natural gel in seconds. Hygiene grade SAP may be preferable, such as SAP sold or provided by Sumitomo™ (Japan). The absorbent core may also include total chlorine free (TCF) fluff pulp, which may be made from long fiber soft woods. In various embodiments of the present disclosure, the combination of hygiene grade SAP and TCF fluff pulp results in a diaper with unexpectedly high absorbency.

Some embodiments can include an acquisition diffusion layer or acquisition distribution layer (ADL) (or transfer layer), covering the absorbent core layer, for example, disposed between the top sheet and the absorbent core layer. Another ADL can be disposed between the back sheet and the absorbent core layer, in some embodiments. The ADL can preferably be nonwoven. The ADL may serve as a layer or covering over the absorbent (SAP+fluff pulp) core layer and helps to diffuse liquids across the absorbent core. The ADL is configured and adapted to diffuse liquids across the layer, pulling moisture away from the bamboo top sheet and/or dispersing moisture across the surface (e.g., across the full foot print) of the absorbent core layer. Liquids released inside the diaper are pulled away from the surface of the top sheet by the moisture-wicking, absorbent properties of the bamboo fiber material, dispersed about the ADL such that the liquid reached proximal and distal portions of the absorbent core layer, where the liquid is absorbed and locked in to the core. The bamboo back layer prevents core material from leaking out of the diaper. ADLs may be thermobonded or thermo-bond (TB) type, hot air through or air through bond type, or other suitable form or type. It may be advantageous to use hot air through ADL, which is low density through air bonded fabrics and are exceptionally efficient in attaining penetration and in preventing rewetting.

Some embodiments can further include an elastic (back) waistband, side leakage guards, and/or a pair of side fasteners (e.g., The elastic back waistband to provide a more comfortable and secure fit. The back waistband may be made of elastic material in order to accommodate a multitude of different shapes and sizes. The side leakage guards can be disposed along the opposing side edges of the top sheet, bottom sheet, core layup, and may prevent waste from leaking out of the diaper. The side leakage guard may comprise or be made of spunbond/meltblown/spunbond (SMS) non-woven material to provide water repellency. The side leakage guard may also, or alternatively, comprise or be made of a polyether-polyurea copolymer (e.g., spandex). The side fasteners can be configured to increase peel force and reinforce the tabs. The side fasteners may be comprised of hook and loop fasteners, or of an adhesive tape with properties allowing for the adhesive tape to be opened and closed repeatedly while still maintain secure closure of the diaper for a prolonged period of time. An example of a suitable side fastener is Avery Dennison® Performance Tape.

The diaper may include front tape, in some embodiments. The front tape may be soft-fluff front tape such as soft-fluff front tape produced by 3M®. The front tape should possess qualities which permit for numerous and frequent opening and closing of the front tape. The front tape may have stiff hooks on one side of the mesh with pliable loops on the opposite side to provide secure closure.

The diapers may also include an optional, disposable booster pad insert, preferably made of natural and/or biodegradable bamboo, incorporated into the diaper, to increase the absorptive capacity of the diaper.

The raw materials used in the diaper may be broken down as follows: 35-40% non-woven fabric, the non-woven fabric may include bamboo fibers, SMS hydrophobic, and hot air hydrophilic, 18-25% super absorbent polymer (SAP), 28-35% paper pulp, 2-8% polyethylene film, and 1-6% adhesives.

In at least one embodiments, the diaper can comprise: (i) about 37% (±10%), w/w, non-woven fabric material, comprising nonwoven bamboo material (e.g., fibers or fiber material), SMS hydrophobic nonwoven material, and/or hot air through hydrophilic nonwoven material; (ii) about 21.5% (±10%), w/w, SAP; (iii) about 31.5% (±10%), w/w, paper pulp; (iv) about 5.5% (±10%), w/w, polyethylene film; and about 4.5% (±10%), w/w, adhesive.

In some embodiments, the material content of the diaper may comprise, consist, or consist essentially of about 12-20% bamboo, by weight. Thus, bamboo may comprise 15-20% of the materials content of the diaper. The total bamboo content may vary with the size of the diaper. A size "small" diaper may comprise 16-20% (±10%), w/w, bamboo fibers, preferably about 18.89%, in some embodiments, based on total materials used. A size "medium" may contain 14-19% (±10%), w/w, bamboo fibers, preferably about 17.19% (±10%), w/w, bamboo fibers, in some embodiments, based on total materials used. Size "large" may contain 12-18% (±10%), w/w, bamboo fibers, preferably about 17.19% (±10%), w/w, bamboo fibers, in some embodiments, based on total materials used.

For example, for any of size small, medium, or large the top sheet may contain about 1-4 g (±10%), w/w, of bamboo, the back sheet may contain 2-5 g (±10%), w/w, of bamboo, for a total of about 3-9 g (±10%), w/w, of bamboo. Illustratively, a size "small" diaper may comprise a top sheet having about 1-3 g (±10%) of bamboo, preferably about 2.166 g (±10%) of bamboo, in some embodiments, a size "medium" diaper may comprise a top sheet having about 1.5-3.5 g (±10%) of bamboo, preferably about 2.512 g (±10%) of bamboo, in some embodiments, and a size "large" diaper may comprise a top sheet having about 1.75-4 g (±10%) or about 2-4 g (±10%) of bamboo, preferably about 2.801 g (±10%) of bamboo, in some embodiments. Similarly, a size "small" diaper may comprise a back sheet having about 2-4 g (±10%) of bamboo, preferably about 3.019 g (±10%) of bamboo, in some embodiments, a size "medium" diaper may comprise a back sheet having about 2.5-4.5 g (±10%) of bamboo, preferably about 3.502 g (±10%) of bamboo, in some embodiments, and a size "large" diaper may comprise a back sheet having about 3-5 g (±10%) of bamboo, preferably about 3.904 g (±10%) of bamboo, in some embodiments. Thus, a size "small" diaper may comprise about 3-7 g (±10%) of bamboo, preferably about 5.185 g (±10%) of bamboo, in some embodiments, a size "medium" diaper may about 4-8 g (±10%) of bamboo, preferably about 6.014 g (±10%) of bamboo, in some embodiments, and a size "large" diaper may comprise about 5-9 g (±10%) of bamboo, preferably about 6.705 g (±10%) of bamboo, in some embodiments.

In one embodiment, the diaper shape may be described as a dumbbell-shaped core. This particular cut may be designed to be form fitting, and may be achieved through the inclusion of an elastic back waistband, a triple stretchable side fastener, super absorbent core, and a 100% bamboo top sheet.

One or more diaper components may be bonded together, in some embodiments. For example, some diaper components may be hot melt (adhesive) bonded.

Diapers are typically worn for extended periods of time, and in some cases it may not be feasible to change a diaper after every rewet. In these cases the diaper must be able to keep the baby dry between rewets. In some embodiments, the amount of SAP typically included in a diaper may be increased and combined with an ADL. The grams per square meter (GSM) of ADL that is needed must be calculated as a function of the SAP ratio used in the core. The higher the SAP ratio, the more GSM needed.

In some embodiments it may be advantageous to increase the peel force of the diapers. This may be achieved by increasing the area of the hooks in the fastening system, increasing the density of hooks per square inch, adding hooks in non-continuous rows of hooks (peak force is typically at the start and end of each row of hooks), or making sure that the hook is compatible with the chosen loop design which may be brushed loops or closed loops.

In some embodiments, to increase the strength of the tab(s), the tab(s) may be reinforced with non-woven material and combined with a hot melt construction adhesive in order to prevent it from breaking if the tab/s is/are pulled hard very quickly.

In some embodiments, a booster pad insert may add additional comfort and leakage protection. The booster pad insert may include additional side protection. The booster pad insert may have a soft natural cotton surface to enhance absorption and an anion strip to neutralize odors and provide antibacterial benefits. The booster pad insert may include sterilized paper which may guide fluids towards a super absorbent polymer gel contained in the core. Super absorbent crystal particles may be present to lock fluids away from the baby's skin and maintain a dry environment. The booster pad insert may include extra sterilized paper to provide 300 degree wrapping protection. The booster pad insert may include a breathable, water-resistant bottom layer which may allow air circulation, and help to eliminate heat and moisture. The absorptive properties of the booster pad insert may cause liquids to be fully absorbed into the booster pad within 60 seconds of the liquid being introduced into the pad, in some embodiments the liquids may be fully absorbed into the pad within 120 seconds of the liquid being introduced to the pad.

Embodiments of the present disclosure may come in multiple sizes to accommodate different sizes and ages of infants and young children. A size "small" diaper may be suitable for a baby weighing 5-10 kg. The total weight of the diaper may be 25-30 g (−/+2 g), and the dimensions may be 365-385 mm×215-245 mm (L×W). A size "medium" diaper may be suitable for a baby weighing 5-12 kg. The total weight of the diaper may be 30-40 g (−/+2 g), and the dimensions may be 415-445 mm×215-245 mm (L×W). A size "large" diaper may be suitable for a baby weighing 8-16 kg. The total weight of the diaper may be 35-45 g (−/+2 g), and the dimensions may be 475-500 mm×215-245 mm (L×W).

Embodiments of the present disclosure are eco-friendly in that they are made of sustainable materials and biodegrade once they are discarded, thereby decreasing landfill waste. Such sustainable and biodegradable materials may include bamboo. Bamboo materials are naturally derived from the bamboo plant, and the bamboo plant itself regenerates quickly once parts of the plant are harvested, rendering its use both economical and sustainable.

Embodiments of the present disclosure are configured to fit snugly around the infant or toddler's thighs and waist to prevent leakage. Embodiments of the present disclosure may be configured in a traditional, open-type, selectively closable, wrap-around diaper style (e.g., having hook-and-loop closures and/or placed on the wearer in an open manner and closed around the body). Alternatively, embodiments of the present disclosure may be "pull up" style for easy application by parents or caregivers, as well as providing an easy means for young children to put them on themselves. The "pull up" style may also provide for snug fitting bands around the thighs and waist of the wearer. The diaper may take a shape similar to an underpant or underwear.

Figure 2:
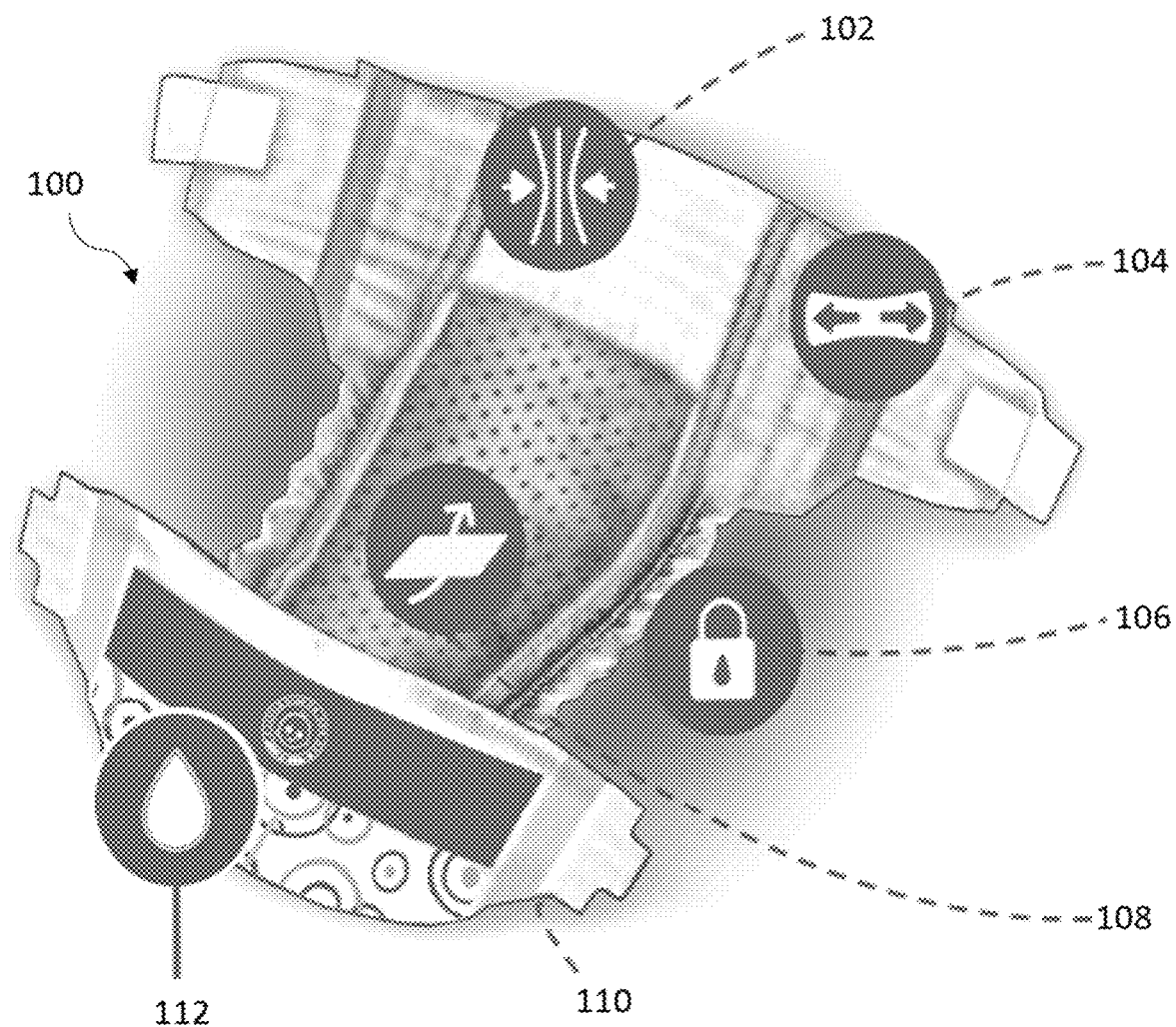
FIG. 2 illustrates a cartoon of the baby diaper of FIG. 1.
Figure 5:
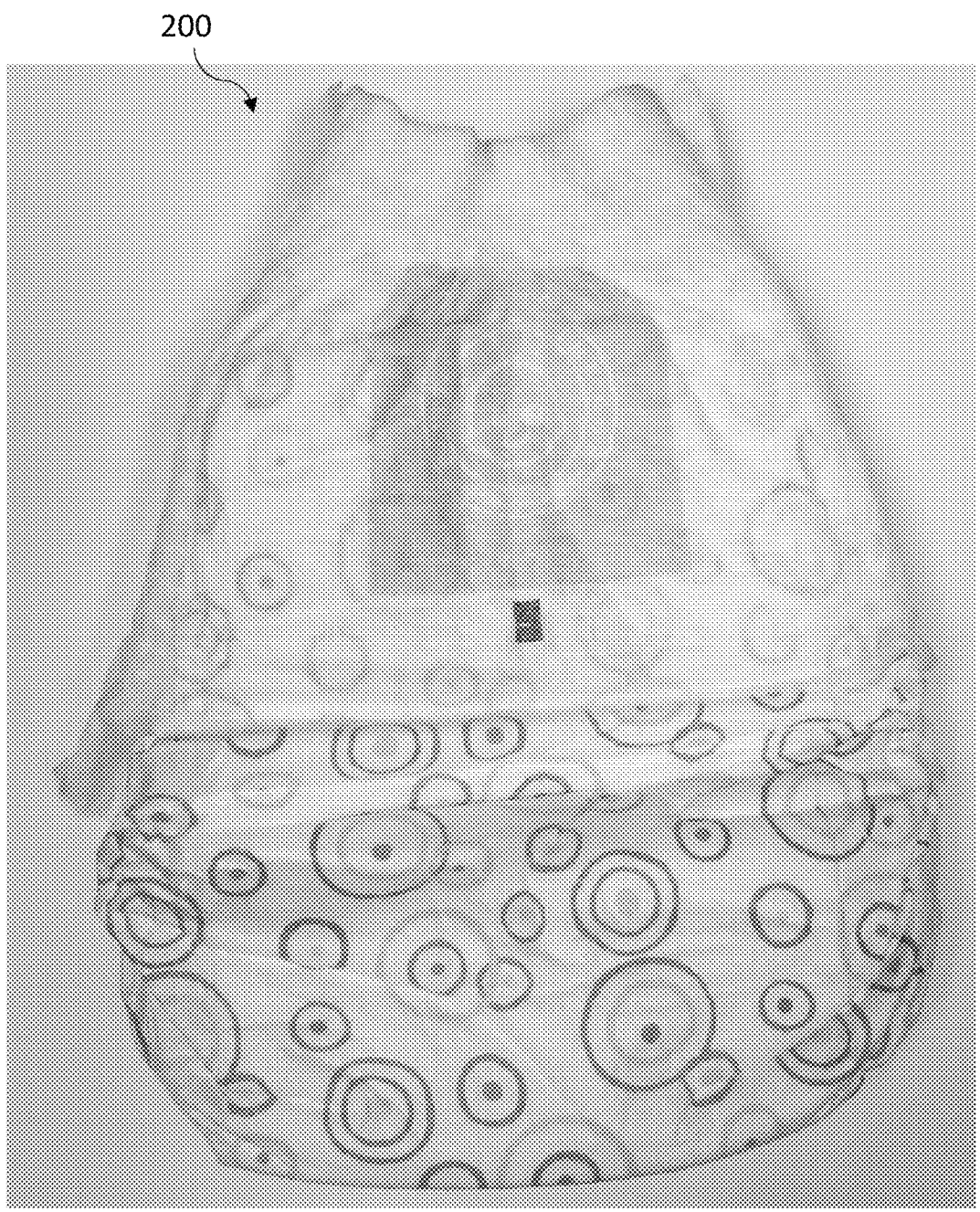
FIG. 5 is a photograph of a swim diaper in accordance with an embodiment of the present disclosure.
Figure 6:
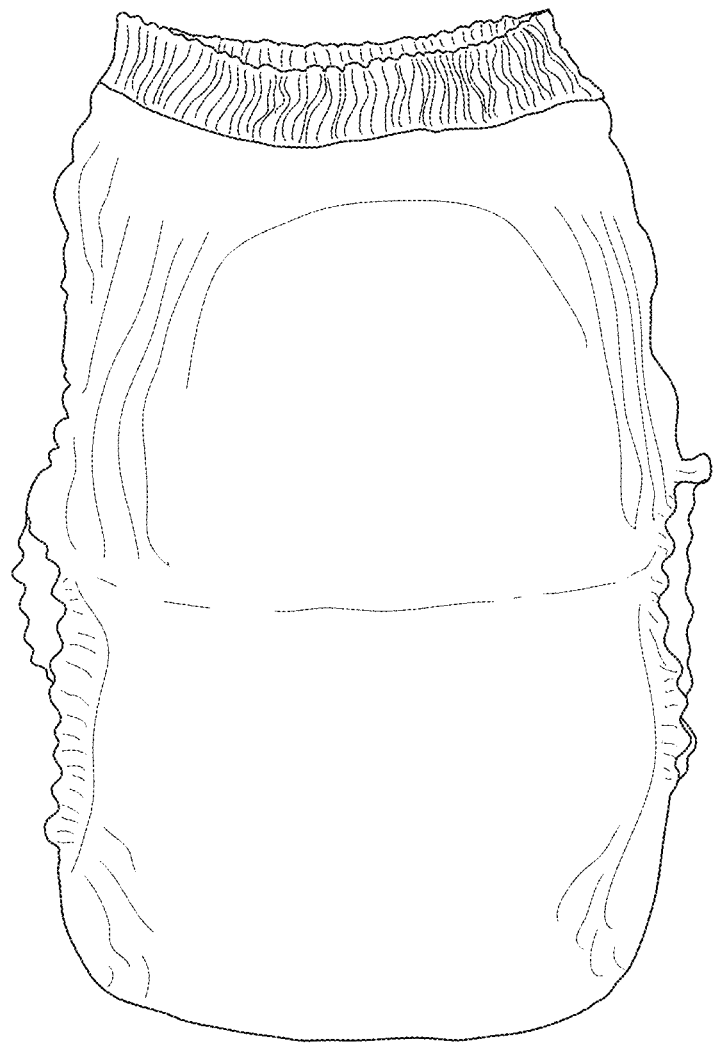
FIG. 6 is a facing view of a first prior art swim diaper.
Figure 7:
FIG. 7 is a facing view of a second prior art swim diaper.

FIGS. 1 and 2 illustrate an exemplary diaper 100 in accordance with an embodiment of the present disclosure. Turning to FIG. 2, it is noted that the reference numbers shown in the drawing do not necessarily identify the precise location of the various elements or components of the exemplary diaper 100. Illustratively, diaper 100 can include an elastic back waistband 102 (which can provide a snug and comfortable fit), stretchable and secure fasteners 104 (which can be comprised of triple stretchable side fasteners to allow the wearer (baby) to move freely, while ensuring a snug, tight, secure fit around the body), a water locking, ultra-absorbent core 106 (comprised of high-quality SAP to keep the diaper's (interior) surface dry by absorbing liquid quickly, creating a water lock), 100% bamboo top sheet and back sheet construction 108 (which is renewable and which is breathable, soft, and silky against the skin, yet extremely strong and absorbent), soft cinched fitted siding 110 (for a fitted, yet gentle protection against leakage), and a wetness indicator 112 (which changes color when wet or when the surrounding pH changes, for example).

Illustratively, the top sheet comprises the outermost layer of the diaper and is made of, form of, and/or comprises 100% bamboo material. The top sheet may include a front tape pattern to impart the diaper with a particular design. The diaper includes leg loops which are intended to sit around or above the thigh of the infant or toddler to provide a comfortable fit (and seal, preventing the contents of the diaper (i.e. fecal matter) from escaping). In some embodiments, the leg loops may include a retention band made from an elastic (polyether-polyurea copolymer) material, such as Lycra, spandex, elastane, or the like to reinforce the leg loops and provide a more secure seal against leakage. The waist band can positioned at the top of the diaper and is intended to sit around the hips or waist of the infant or toddler. The waist can also serve as a seal, similar to the leg loops, in that it prevents the contents of the diaper from escaping. In some embodiments, the waist band can be reinforced with a retention band to reinforce the waist and provide a more secure seal. The retention bands can be thick or thin depending on the size of the infant or the materials used or on a particular design preference. Thin retention bands may be ideal for smaller infants and to provide more room within the diaper. Larger retention bands which comprise a larger portion of the diaper may provide a more effective seal against leakage.

The interior of the diaper includes a back sheet. The back sheet may be made of spun-melt-spun (SMS), non-woven, cloth-like, breathable, 100% bamboo material. Contained between the back sheet and the top sheet, is the absorbent core layer. The inner most layer which comes into contact with the wearer is the back sheet. The outermost layer, the top sheet comprises the outside of the diaper. Contained between the back sheet and the top sheet is the absorbent core. The absorbent core may be (wrapped airlaid) fluff material with super absorbent polymer (SAP) in order to absorb and contain the contents of the diaper.

Physical evaluation of illustrative diapers in accordance with the present disclosure provides additional description of various aspects of the certain embodiments. As outlined in Table 1, for example, five (5) diapers (A, B, C, D, E) in accordance with the present disclosure. Illustratively, the diapers may have a target production weight of 40 grams and may range in product weight (whole diaper weight) by as much as 0.59 g (between about 39.37 g and about 40.83 g). It is noted that the variability of product weight is world-class for fluff-containing diapers. Additional product weight variation may also be common. For example, diapers (in the same lot or product production run) may vary in total, whole diaper weight by up to 1 g without necessarily departing from the scope of the present disclosure. Moreover, diaper weight (e.g., in grams) may depend on the size of the diaper (or intended wearer). Thus, infant diapers, small diapers, medium diapers, large diapers, and/or x-large diapers may (all) be of different size and/or weight.

TABLE 1

| Diaper | Weight (g) |
| --- | --- |
| A | 40.83 |
| B | 40.44 |
| C | 40.62 |
| D | 39.37 |
| E | 39.89 |
| Mean | 40.23 |
| Standard Deviation | 0.59 |

Turning now to FIG. 3, an illustrative diaper (exterior) in accordance with the present disclosure is shown. The diaper exterior can comprise a cloth-like back sheet comprising a two-ply laminate of nonwoven material mated to a polyethylene film. The landing zone (for the hook-and-loop fasteners), closure tabs, stretch closure tabs, stretchable waist band, and wetness indicator are each shown and labeled. That landing zone can be a cut-and-place nonwoven loop laminated to a poly strip. Illustrative diaper dimensions in FIG. 3 are 167×44 mm.

The top sheet can comprise (or be comprised of) bamboo-derived fibers. Illustratively, the top sheet basis weight can be about 40 grams per square meter (gsm). This value is considerably heavier than most commercial diapers, particularly in the U.S./Canadian market where values of 12-18 gsm are common.

In FIG. 4, an illustrative diaper interior is presented. The interior of the diaper (see FIG. 4) includes the following, non-limiting diaper elements: standing inner leg gathers (typically made of three ply nonwovens: spunbond/meltblown/spundbond), a nonwoven top sheet and a visible acquisition and distribution layer (ADL) just below the topsheet. The core shape is evident and can be described as "hour-glass" shape.

The inner leg gathers, for example, can be tacked down over a 95 mm distance from the back of the diaper and 80 mm from the front of the diaper. This tack down ensures that the inner leg gathers will "stand" in the worn configuration, forming a "bucket" for fluid to be retained before it is fully absorbed by the core materials. In addition to the inner leg gathers, which illustratively can have two spandex strands to provide elasticity, there can be two strands of elastic running on each side of the diaper center that provide further fit elasticity around the legs (leg gathers) and there can also be a stretch film incorporated into the waist at the back of the diaper to improve fit around the waist.

Illustratively, opening the diaper chassis allows access to the interior of the diaper that comprises the ADL, the tissue core wrap, and the core, which is a blend of fluff fibers and superabsorbent polymer (SAP). The core weight can be determined with reasonable accuracy by physically removing the fluff and SAP, as much as possible, and weighing these materials. Removing the fluff and SAP from the diaper provides a very good approximation of the weight of the remaining components of the diaper interior (ADL, nonwovens, spandex, adhesive, etc), which is termed the "surrounds".

Table 2 presents the so-called "core" weight of the five (5) illustrative diapers.

TABLE 2

| Diaper | Core Weight (g = Diaper Weight −18.00 g) |
| --- | --- |
| A | 22.83 |
| B | 22.44 |
| C | 22.62 |
| D | 21.37 |
| E | 21.89 |
| Mean | 22.23 |

As shown in Table 2, the surrounds weight does not vary much (e.g., since these materials are carefully fed to the machine from precision rolls of materials or from precise metering of adhesives). Thus, the approximate weight of the surrounds allows us to have some measure of the variability of the weight of the core, which, by the nature of its inclusion into the diaper, tends to have higher variability than other materials. The surrounds weight for a single diaper was measured at 18.00 g. The approximated core weights are given in Table 2.

The cores can be air formed cores, made on a rotating drum (drum former) under mild vacuum conditions (other air laid technology exists, but is very rarely used for high-speed core formation).

Table 3 presents the approximate core weight distribution (in the diapers). By taking the average core weight and dividing by the area of the core (0.041 m2), the core basis weight is approximately 540 gsm. This is the average basis weight. By dividing the core into sections, one can determine if the core materials are distributed evenly along the length of the core or if there are some portions of the core with more or less mass per unit area. This distribution is termed the "3D profile". This measurement is difficult and, at best, approximate, but it does show mass distribution trends (Table 3).

TABLE 3

| Section (approximate size) | Core Weight (rounded to nearest 10 gsm) |
| --- | --- |
| A (115 × 50 mm) | 570 |
| B (112.5 × 50 mm) | 610 |
| C (102.5 × 50 mm) | 590 |
| D (92.5 × 50 mm) | 520 |
| E (105 × 50 mm) | 500 |
| F (115 × 50 mm) | 560 |
| G (120 × 70 mm) | 540 |

As shown in Table 3, in some embodiments, the basis weight of zones B and C, near the front of the diaper, may contain more absorbent material than the rest of the diaper. This distribution of absorbent material is common (i.e., a normal mass distribution for a 3D-profiled absorbent core).

The SAP can be ultra-high quality. Swelling tests (e.g., swelling the core in 0.9% saline) can be used to show that there is a substantial amount of SAP in the core. Under magnification, the swollen SAP form an agglomeration (or mass) of beads or spheres.

The ADL can be a highloft nonwoven. Illustratively, the ADL can be resin bonded or through-air bonded (preferably through-air bonded). The ADL can have a basis weight of 44 gsm (adhesive weight not included). The basis weight range of 40-45 gsm can be common in certain embodiments.

In an illustrative manufacturing method of the exemplary diapers, fluff pulp can be fed through a hammer mill to produce fiber bundles that are sent into a chamber where the fluff is mixed with SAP that is metered into the same chamber. The chamber can include a rotating surface (drum former) that is under mild vacuum and equipped with screens to allow the passage of air and the retention of the mixed fluff and SAP. Mixing of fluff and SAP may not be perfectly uniform, so there may be portions of the core that have higher concentrations of either fluff or SAP (this can be verified by dosing the core with 0.9% saline and observing the swelling of the SAP). Nonuniform cores may show pockets of SAP within the fluff and SAP mix.

In some embodiments, the diaper core (with its sharp leading and trailing edges) is formed continuously in 3D-profiled "pockets" and cut after the core is transferred to the conveyor on the diaper machine. The core is formed on tissue, and the tissue is placed on the conveyor, where it is wrapped and cut and then compressed (debulked), preferably in a single step. The core wrap is sealed on the upper surface of the core (nearest the wearer) with adhesive. In rapid succession, the wrapped core is placed on the back sheet through differential speeds on the feed conveyor and the back-sheet conveyor. The wetness indicator is applied to (printed on) the inner surface of the back sheet just before the core is placed on the back sheet. In other words, the wetness indicator on the PE layer, which is in the next layer of bottom nonwoven. Accordingly, this layer is not in contact with skin, directly The printed wetness indicator is further made from plant-based material.

The ADL and closure tabs are then added to the diaper and the topsheet and leg gathers are added. The assembly is cut to individual diapers, which are then folded and packaged.

Table 4 presents the results of absorption capacity testing of the diapers of the present disclosure. Sample A (ALT) is an inventive diaper according to embodiments of the present disclosure. Sample B (BH) is a leading diaper advertised as having a bio-based core of sustainably-harvested fluff pulp and plant-derived materials. Sample C (CPP) is a leading diaper advertised as having soft plant-based and other thoughtfully selected materials and 0% chlorine bleaching, fragrances, parabens, latex.

In testing the absorption capacity of the diapers, the total amount of fluid a diaper can hold is measured in grams. After soaking the diapers in a saline solution, which is the closest representation of human urine, for 30 minutes the diapers of the present disclosure, with an average dry weight of 39.9 grams absorbed between 904-969 grams of liquid, with an average of 936 grams of liquid. Thus, the diapers of the present disclosure absorb, on average, 23.5 times their dry weight, in liquid. This demonstrates a higher absorbency performance of the inventive diapers over the leading traditional and natural diapers tested.

TABLE 4

|  | Sample ALT | Sample BH | Sample CPP |
|---|---|---|---|
| Dry Weight (g) | | | |
| 1 | 41.0 | 25.8 | 28.7 |
| 2 | 39.6 | 24.5 | 28.6 |
| 3 | 38.9 | 24.3 | 28.2 |
| 4 | 39.9 | 29.2 | 29.3 |
| 5 | NA | 30.2 | 28.6 |
| Average | 39.9 | 26.8 | 28.7 |
| Std. Dev. | 0.87 | 2.73 | 0.40 |
| Maximum | 41.0 | 30.2 | 29.3 |
| Minimum | 38.9 | 24.3 | 28.2 |
| n= | 4 | 5 | 5 |
| Absorption Capacity (g) | | | |
| 1 | 969 | 542 | 504 |
| 2 | 923 | 511 | 520 |
| 3 | 904 | 522 | 514 |
| 4 | 949 | 650 | 521 |

TABLE 4-continued

|  | Sample ALT | Sample BH | Sample CPP |
|---|---|---|---|
| 5 | NA | 663 | 505 |
| Average | 936 | 578 | 513 |
| Std. Dev. | 28.6 | 73.1 | 7.9 |
| Maximum | 969 | 663 | 521 |
| Minimum | 904 | 511 | 504 |
| n= | 4 | 5 | 5 |

The speed of the absorbency is also an important factor. Table 5 presents the results of Strike-Through testing of the diapers of the present disclosure. Sample A-LT is the inventive diaper according to embodiments of the present disclosure. Sample B-H is a first leading conventional. Sample C-P is a second leading conventional diaper. Sample BH is the leading diaper advertised as having a bio-based core of sustainably-harvested fluff pulp and plant-derived materials. Sample CPP is the leading diaper advertised as having soft plant-based and other thoughtfully selected materials and 0% chlorine bleaching, fragrances, parabens, latex.

TABLE 5

|  | Sample A-LT | Sample B-H | Sample C-P |
|---|---|---|---|
| Liquid Strike-Through Rate (s) | | | |
| Average | 8.64 | 64.77 | 162.35 |
| Std. Dev. | 1.826 | 12.556 | 70.852 |
| Maximum | 12.53 | 81.99 | 266.83 |
| Minimum | 6.24 | 42.89 | 57.99 |
| n= | 10 | 10 | 10 |
| Rate for second insult (s) | | | |
| Average | 17.57 | 85.44 | 138.03 |
| Std. Dev. | 2.419 | 15.453 | 42.976 |
| Maximum | 21.50 | 111.18 | 203.05 |
| Minimum | 14.10 | 54.19 | 72.53 |
| n= | 10 | 10 | 10 |
| Rate for third insult (s) | | | |
| Average | 18.56 | 77.46 | 136.07 |
| Std. Dev. | 2.829 | 9.884 | 64.073 |
| Maximum | 23.63 | 92.22 | 287.41 |
| Minimum | 14.85 | 55.66 | 77.15 |
| n= | 10 | 10 | 10 |

|  | Sample BH | Sample CPP |
|---|---|---|
| Liquid Strike-Through Rate (s) | | |
| Average | 82.49 | 114.96 |
| Std. Dev. | 74.523 | 78.867 |
| Maximum | 276.10 | 320.83 |
| Minimum | 31.58 | 57.74 |
| n= | 10 | 10 |
| Rate for second insult (s) | | |
| Average | 118.33 | 122.06 |
| Std. Dev. | 119.818 | 51.083 |
| Maximum | 443.78 | 210.12 |
| Minimum | 43.59 | 67.88 |
| n= | 10 | 10 |
| Rate for third insult (s) | | |
| Average | 67.21 | 120.99 |
| Std. Dev. | 19.201 | 43.685 |
| Maximum | 90.41 | 221.26 |
| Minimum | 33.14 | 68.41 |
| n= | 10 | 10 |

The Liquid Strike-Through test measures the rate (in seconds) that fluid is absorbed into the core. As presented in Table 5, it took an average of 8.64 seconds for the liquid to be absorbed into the core of the inventive diaper according to embodiments of the present disclosure. This far exceeds the average performance of the leading traditional and "natural" brands of diapers, which on average ranged from a minimum of 82.49 seconds to a maximum 114.96 seconds. The quicker the fluid is absorbed into the core the longer the top sheet can remain dry. Having a quicker absorption rate gives the diapers of the present disclosure advantages over traditional and natural diapers.

The inventive bamboo diapers provide several advantages over prior art diapers. The inventive diaper top sheet and back sheet are made from 100% bamboo fibers as opposed to other natural brands that may use a combination of other plant materials, such as cotton, corn, sugarcane, and wheat. These bi-products may cause an allergic reaction as some babies have sensitivity to wheat, corn and other natural ingredient bi-products. Moreover, the inventive diapers are free of other (chemical) irritants, such as chlorine, alcohol, perfumes or fragrances, phthalates, parabens, latex, epoxy, polyvinyl chloride (PVC), tributyltin (TBT), bisphenol (BPA), 2-mercaptobenzothiazole (MBT), dibenzothiophene (DBT), antioxidants, surfactants, detergents, and/or preservatives, which have been shown to cause dermatitis and/or other skin reactions, especially in babies with sensitive skin.

As shown above, the absorptive capacity and speed of the inventive diapers are greater than those of existing diapers. Having a quicker absorption rate and a great absorptive capacity gives the diapers of the present disclosure advantages over traditional and natural diapers (e.g., made from cotton fibers or other plant-based materials).

When used in a top and back diaper sheet, bamboo fibers wicking ability pulls moisture away from the baby's skin, providing faster dry comfort and more longevity of the diaper, making them great for either day or overnight use. A more absorbent diaper creates a healthier diaper as moisture is one of the main causes of skin irritations such as the more common diaper rash. In addition, bamboo is naturally hypoallergenic, moisture and thermal regulating, and has deodorizing and antibacterial properties.

The manufacturing process of the diaper core also contributes to the diaper's performance when it comes to absorbency. The diaper core is formed continuously in 3D-profiled "pockets", and cut after the core is transferred to the conveyor on the diaper machine. The core is formed on tissue, and the tissue is placed on the conveyor, where it is wrapped and cut and then compressed (debulked) in a single step. The core wrap is sealed on the upper surface of the core (nearest the wearer) with adhesive. In rapid succession, the wrapped core is placed on the back sheet through differential speeds on the feed conveyor and the back sheet conveyor. The adhesive wetness indicator is applied to the inner surface of the back sheet just before the core is placed on the back sheet.

At least one reason and benefit of using this method of core wrap is to prevent SAP particles from coming out of the core. This reduces the occurrence of the puncturing of the back sheet which can happen due to direct contact of the SAP during the compression of the diaper. The core wrap also improves fluid wicking for the initial encounter of the core with urine. The combination of bamboo and the core wrap improves the diaper's ability to absorb more fluid at a faster pace than the leading natural diapers on the market today.

Natural Swim Diapers

Some embodiments of the present disclosure enable the manufacture of natural disposable swim diapers (see FIGS. 5-14). Swim diapers, while not generally designed to help babies stay feeling dry, still benefit from the use of natural, eco-friendly, and/or sustainable materials. Embodiments of the present disclosure are eco-friendly in that they are made of sustainable materials and biodegrade once they are discarded, thereby decreasing landfill waste, rendering its use both economical and sustainable. The swim diapers of the present disclosure do not include bamboo, pulp, water crystals, or other water-logging material(s). However, the diapers still have an absorbent material to trap urine.

Some embodiments may comprise a top sheet, a front tape pattern, an absorbent core, a back sheet, and a waist band. The top sheet may be a hot calendaring top sheet to provide a smooth, durable surface. A front tape pattern may be achieved through the use of tissue paper having printed patterns. The absorbent core may be made of air-laid tissue paper. Air laid tissue paper is a nonwoven fabric made from long fiber softwood fluff puff. It is bulky, porous and soft with good water absorption properties. The back sheet may be made of any non-toxic, odorless, and water-resistant material such as SMS non-woven fabric. Certain non-woven fabrics may prevent the spread of bacteria. Non-woven fabrics are preferred for their water repellency and cloth-like, breathable feel. The waistband may be made of any non-toxic material with elastic properties such as Lycra, Spandex, elastane and the like.

The swim diaper includes a back sheet, which comprises the outermost layer of the diaper. The back sheet may include a front tape pattern to impart the diaper with a particular design. The swim diaper includes leg loops which are intended to sit around or above the thigh of the infant or toddler to provide a seal preventing the contents of the swim diaper (i.e. fecal matter) from escaping. In some embodiments, the leg loops may include a retention band made from an elastic material such as Lycra, spandex, or the like to reinforce the leg loops and provide a more secure seal against leakage. A waist loop is positioned at the top of the swim diaper and is intended to sit around the hips or waist of the infant or toddler. The waist loop serves as a seal, similar to the leg loops, in that it prevents the contents of the swim diaper from escaping. In some embodiments, the waist loop may be reinforced with a retention band to reinforce the waist loop and provide a more secure seal. The retention bands may be thick or thin depending on the size of the infant or the materials used or on a particular design preference. Thin retention bands may be ideal for smaller infants and to provide more room within the diaper. Larger retention bands which comprise a larger portion of the diaper may provide a more effective seal against leakage.

Through the leg loop, the interior of the diaper is visible which includes a top sheet. The inner most layer which comes into contact with the wearer is the top sheet. The top sheet may be made of SMS non-woven, cloth-like, breathable material. Contained between the back sheet and the top sheet, is the absorbent core layer. The top sheet may be made of SMS non-woven, cloth-like, breathable material. Contained between the back sheet and the top sheet, is the absorbent core layer. The absorbent core may be wrapped airlaid tissue with or without fluff, without super absorbent polymer (SAP), etc., in order to contain the contents of the swim diaper without absorbing and becoming weighed down with water in an aqueous environment.

The swim diapers can also be substantially free or devoid of irritants, including harsh chemicals, such as chlorine, alcohol, perfumes or fragrances, phthalates, parabens, latex, epoxy, polyvinyl chloride (PVC), tributyltin (TBT), bisphenol (BPA), 2-mercaptobenzothiazole (MBT), dibenzothiophene (DBT), sugar cane, wheat or wheat by-products, corn or corn by-products, antioxidants, surfactants, detergents, and/or preservatives, which have been shown to cause dermatitis and/or other skin reactions, especially in babies with sensitive skin.

An exemplary list of swim diaper components and acceptable, illustrative materials thereof is presented in Table 6, below.

TABLE 6

| No | Material Name | Material Characteristics/model |
|---|---|---|
| 1 | Surface Non-woven | Hot-rolled hydrophilic Non-woven |
| 2 | Absorbent Paper | Air-laid Paper |
| 3 | Wrapped Non-woven | Spunbonded hydrophilic non-woven |
| 4 | Printed Breathable PE Film | D8WW |
| 5 | Back Sheet Non-woven | Softer Spunbonded non-woven S.S |
| 6 | Inside Waistband Non-woven | Softer Spunbonded non-woven S.S |
| 7 | Outside Waistband Non-woven | Softer Spunbonded non-woven S.S |
| 8 | Printed Front Logo | Tissue |
| 9 | Prevent leakage non-woven | SMMS Water repellent Non-woven |
| 10 | Elastics (Waistband, leak-guard, legs) | Spandex Silk |

In some embodiments, the swim diaper may take a shape similar to an underpant, underwear, or swim bottom. The waistband and leg holes may be A top sheet may comprise the outermost layer of the swim diaper with the front tape pattern wholly or partially overlaid on top of the top sheet to impart a design or pattern.

In some embodiments, the swim diaper components may comprise non-woven fabric, airlaid tissue paper, Spandex and/or Lycra, polyethylene film, and adhesives. In some embodiments the non-woven fabric may comprise 30.0-40.0 wt. % of the total swim diaper composition, more preferably 35.0-45.0 wt. %, more preferably 40.0-50.0 wt. %, more preferably 45.0-55.0 wt. %. In some embodiments the airlaid tissue paper may comprise 20.0-30.0 wt. % of the total swim diaper composition, more preferably 30.0-40.0 wt. %, more preferably 35.0-45.0 wt. %. In some embodiments the Spandex and/or Lycra may comprise 0.01-2.0 wt. % of the total swim diaper composition, more preferably 2.0-3.0 wt. %, more preferably 3.0-4.0 wt. %. In some embodiments the polyethylene film may comprise 2.0-3.0 wt. %, more preferably 3.0-4.0 wt. %, more preferably 4.0-5.0 wt. %, more preferably 5.0-6.0 wt. %, more preferably 6.0-7.0 wt. %. In some embodiments the adhesives may comprise 5.0-10.0 wt. % of the total swim diaper composition, more preferably 10.0-20.0 wt. %, more preferably 20.0-30.0 wt. %.

Embodiments of the swim diaper of the present disclosure are configured to fit snugly around the infant or toddler's thighs and waist to prevent leakage. Embodiments of the present disclosure do not contain water crystals; therefore, they will not absorb water when worn by a user while submerged in water or swimming. Embodiments of the present disclosure may be "pull up" style for easy application by parents or caregivers, as well as providing an easy means for young children to put them on themselves. The "pull up" style may also provide for snug fitting bands around the thighs and waist of the wearer.

Embodiments of the present disclosure may come in multiple sizes to accommodate different sizes and ages of infants and young children. A size "small" diaper may be suitable for a baby weighing 5-10 kg. The total weight of the swim diaper may be 22-26 g (−/+2 g), and the dimensions may be 440-470 mm×380-395 mm (L×W). A size "medium" diaper may be suitable for a baby weighing 8-14 kg. The total weight of the swim diaper may be 22-26 g (−/+2 g), and the dimensions may be 460-490 mm×380-395 mm (L×W). A size "large" diaper may be suitable for a baby weighing 10-16 kg. The total weight of the swim diaper may be 22-26 g (−/+2 g), and the dimensions may be 490-510 mm×380-395 mm (L×W).

An illustrative set of diapers, by size, are presented in Table 7, below.

TABLE 7

Swimmy Diaper Specs

| Size | L × W (mm) | Total Weight (g) | Baby Weight |
|---|---|---|---|
| S | 460*390 | 24 ± 2 g | 6-10 kgs<br>13-22 lbs |
| M | 480*390 | 24 ± 2 g | 9-14 kgs<br>19-30 lbs |
| L | 500*390 | 24 ± 2 g | >12 kgs<br>>26 lbs |

A breakdown of exemplary raw materials is presented in Table 8, below.

TABLE 8

| Breakdown of Main Raw Material | Rate |
|---|---|
| Nonwoven Frabic | 45.0% |
| * Airlaid Tissue Paper | 34.0% |
| Spandex (Lycra) | 2.5% |
| Polyethylene film | 5.5% |
| Adhesives | 13.0% |
| Total | 100.0% |

Figure 8:
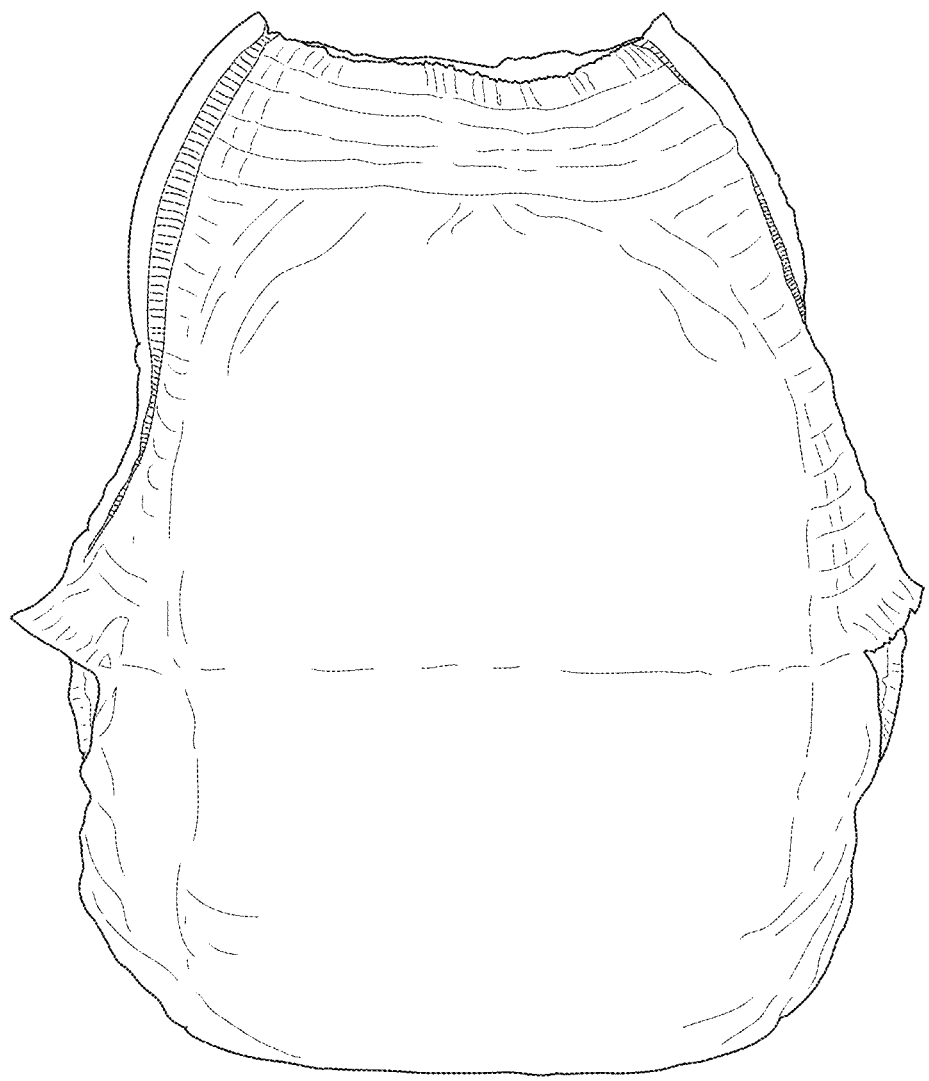
FIG. 8 is a facing view of a swim diaper in accordance with an embodiment of the present disclosure.
Figure 9:
FIG. 9 is a perspective view of the swim diaper of FIG. 1.
Figure 10:
FIG. 10 is a rear view of the swim diaper of FIG. 1.
Figure 11:
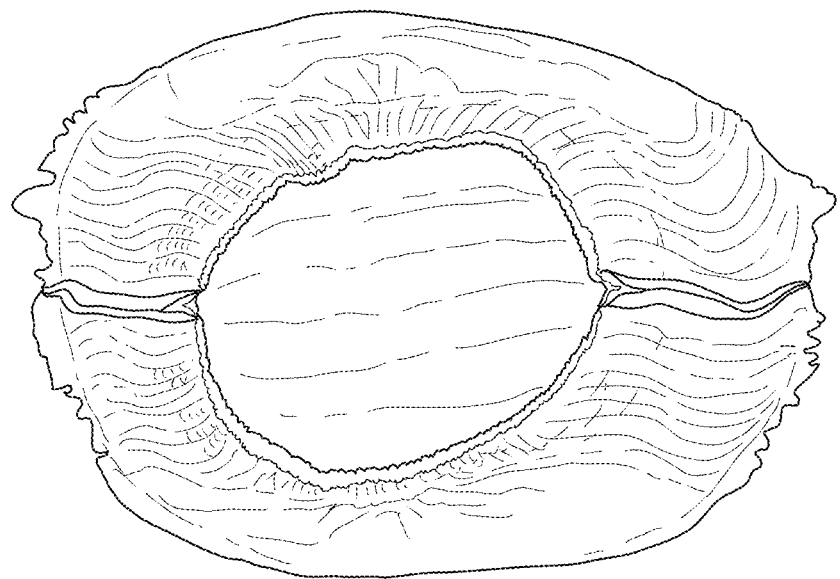
FIG. 11 is a top view of the swim diaper of FIG. 1.
Figure 12:
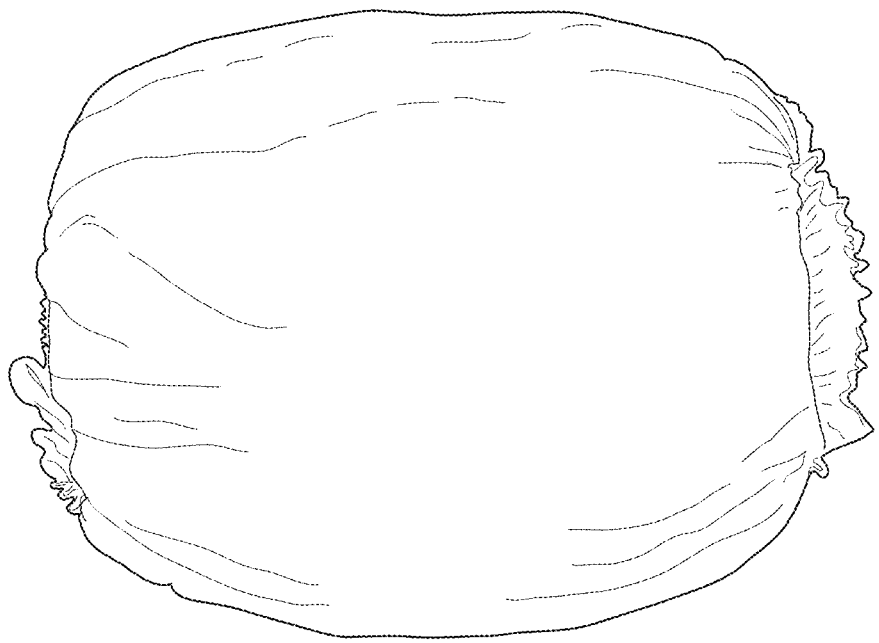
FIG. 12 is a bottom view of the swim diaper of FIG. 1.
Figure 14:
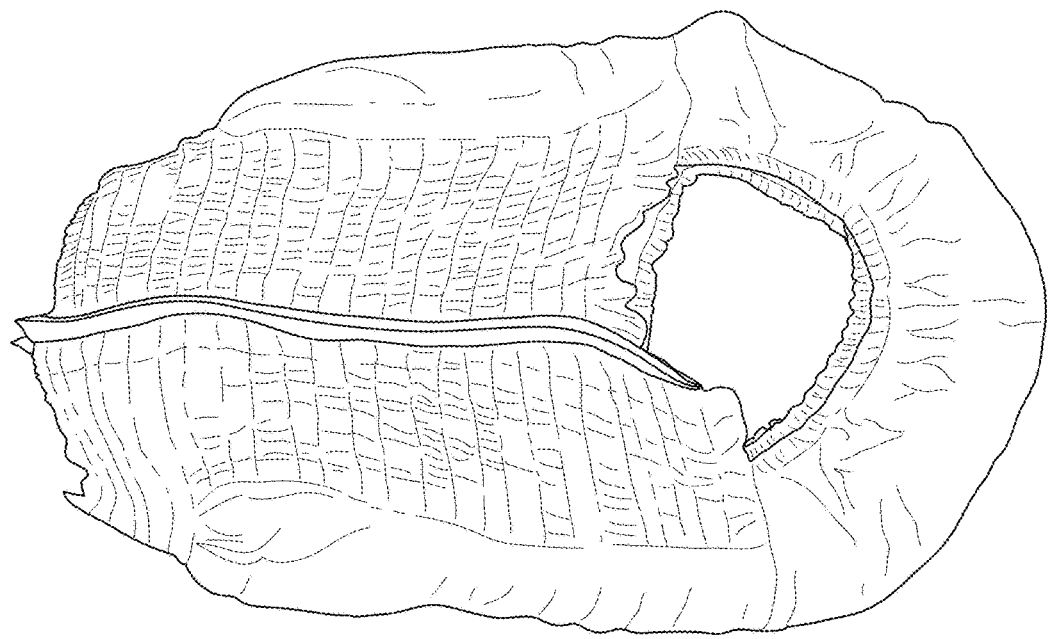
FIG. 14 is a left side view of the swim diaper of FIG. 1.
Figure 13:
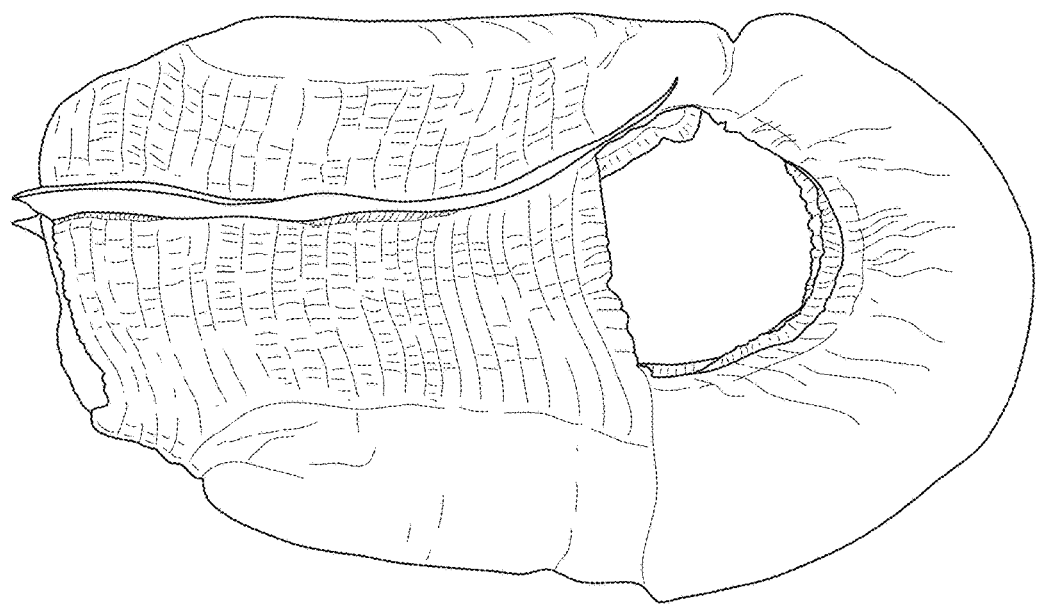
FIG. 13 is a right side view of the swim diaper of FIG. 1.

In at least one embodiment, as depicted best in FIG. 8, the diaper can have a wide bottom (seat) portion. The rounded bottom gives the swim diaper a fuller coverage and can provide better protection against leaks. The roundness of the bottom also provides a more comfortable fit with softer edges. The softer edges reduce the need of more elasticity around the leg cuffs, which also increase the containment giving a more secure fit. Unlike existing diapers (see FIGS. 6 and 7) made with traditional materials that seek to enhance comfort by reducing the width of the diaper at the base (between the baby's legs), the ultra-soft material of the diapers of the present disclosure provides added material comfort, allowing the base of the diaper to be widened, retaining comfort without sacrificing coverage.

CONCLUSIONS

The disclosed and/or described embodiments are to be considered in all respects only as illustrative and not restrictive. While various aspects, features and embodiments have been disclosed herein, other aspects, features and embodiments are contemplated but may not be disclosed. For instance, certain well-known aspects, features and embodiments are not described herein in particular detail in order to avoid obscuring aspects of the described embodiments. Such aspects, features and embodiments are, however, contemplated herein. Thus, while a number of methods and components similar or equivalent to those described herein can be used to practice embodiments of the present disclosure, only certain components and methods are described herein.

The present disclosure may also be embodied in other specific forms without departing from its spirit or essential characteristics. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. For instance, various alterations and/or modifications and additional applications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure.

It will be appreciated that certain embodiments (e.g., compositions, formulations, method, etc.) may include, incorporate, or otherwise comprise features (e.g., properties, components, ingredients, elements, parts, portions, steps, etc.) described in other embodiments disclosed and/or described herein. Accordingly, the various features of certain embodiments can be compatible with, combined with, included in, and/or incorporated into other embodiments of the present disclosure. Thus, disclosure of certain features relative to a one embodiment of the present disclosure should not be construed as limiting application or inclusion of said features to the specific embodiment. Rather, it will be appreciated that other embodiments can also include said features without necessarily departing from the scope of the present disclosure. Moreover, unless a feature is described as requiring another feature in combination therewith, any feature herein may be combined with any other feature of a same or different embodiment disclosed herein.

The scope of the invention is, therefore, indicated by the appended claims rather than by the foregoing description. All changes which come within the meaning and range of equivalency of the claims are to be embraced within their scope.

What is claimed is:

1. A natural baby diaper, comprising:
   a top sheet comprising 100% bamboo fiber;
   a back sheet comprising 100% bamboo fiber;
   an absorbent core disposed between the top sheet and the back sheet, the absorbent core comprising super absorbent polymer (SAP); and
   an acquisition distribution layer (ADL) covering the absorbent core;
   wherein the diaper is substantially free or devoid of chlorine, alcohol, perfume or fragrance, phthalate, latex, epoxy, polyvinyl chloride (PVC), tributyltin (TBT), bisphenol (BPA), 2-mercaptobenzothiazole (MBT), dibenzothiophene (DBT), antioxidant, surfactants, detergents, and/or preservative,
   wherein the diaper comprises, by weight:
   12-20% bamboo fibers;
   18-25% SAP;
   28-35% paper pulp;
   2-8% polyethylene film; and
   1-6% adhesive.

2. The diaper of claim 1, further comprising:
   an elastic waistband;
   side leakage guards; and
   a pair of side fasteners.

3. The diaper of claim 1,
   wherein the top sheet and back sheet form a dumbbell shape of the diaper and the absorbent core is situated in a seat portion of the diaper to collect fluids and/or waste,
   the diaper further comprising a front tape on an anterior portion of an outer side of the top sheet;
   one or more side fasteners affixed to one or more sides of the diaper;
   a back waistband on a top of a posterior portion of the diaper; and
   one or more side leakage guards surrounding one or more extremity openings.

4. The diaper of claim 3, wherein the bamboo fibers are 100% biodegradable.

5. The diaper of claim 1, wherein the top sheet and back sheet form a dumbbell shape of the diaper and the absorbent core is situated in a seat portion of the diaper to collect fluids and/or waste.

6. The diaper of claim 1, further comprising:
   a front tape on an anterior portion of an outer side of the top sheet;
   one or more side fasteners affixed to one or more sides of the diaper;
   a back waistband on a top of a posterior portion of the diaper; and
   one or more side leakage guards surrounding one or more extremity openings.

7. The diaper of claim 1, further comprising:
   spunbond/meltblown/spunbond (SMS) hydrophobic material; and
   hot air hydrophilic material.

8. A natural baby diaper, comprising:
   a top sheet comprising 100% bamboo fiber;
   a back sheet comprising 100% bamboo fiber;
   an absorbent core disposed between the top sheet and the back sheet, the absorbent core comprising super absorbent polymer (SAP);
   an acquisition distribution layer (ADL) covering the absorbent core;
   a front tape on an anterior portion of an outer side of the top sheet;
   one or more side fasteners affixed to one or more sides of the diaper;
   a back waistband on a top of a posterior portion of the diaper; and
   one or more side leakage guards surrounding one or more extremity openings,
   wherein the diaper is substantially free or devoid of chlorine, alcohol, perfume or fragrance, phthalate, latex, epoxy, polyvinyl chloride (PVC), tributyltin (TBT), bisphenol (BPA), 2-mercaptobenzothiazole (MBT), dibenzothiophene (DBT), antioxidant, surfactants, detergents, and/or preservative,
   wherein the top sheet and back sheet form a dumbbell shape of the diaper and absorbent core is situated in a seat portion of the diaper to collect fluids and/or waste,
   wherein the diaper comprises, by weight:
   12-20% bamboo fibers;
   18-25% SAP;
   28-35% paper pulp;
   2-8% polyethylene film; and
   1-6% adhesive.

9. The diaper of claim 8, further comprising:
   spunbond/meltblown/spunbond (SMS) hydrophobic material; and
   hot air hydrophilic material.

* * * * *